United States Patent [19]
Drucker et al.

[11] Patent Number: 5,194,249
[45] Date of Patent: Mar. 16, 1993

[54] NON-WHITENING ANTIPERSPIRANT COMPOSITIONS

[75] Inventors: Jacob Drucker, Holmdel; Gianluigi Soldati, Edison, both of N.J.

[73] Assignee: Carter-Wallace, Inc., New York, N.Y.

[21] Appl. No.: 601,167

[22] Filed: Oct. 19, 1990

[51] Int. Cl.$^5$ ............................ A61K 7/34; A61K 7/38
[52] U.S. Cl. ......................................... 424/68; 424/66
[58] Field of Search ..................................... 424/68, 66

[56] References Cited

U.S. PATENT DOCUMENTS 4,551,330 11/1985 Wagman et al. ...................... 424/68
4,719,103 1/1988 Krevald et al. .............. 424/DIG. 5
4,948,578 8/1990 Burger et al. ................ 424/DIG. 5

Primary Examiner—Dale R. Ore
Attorney, Agent, or Firm—Kevin B. Clarke

[57] ABSTRACT

Aqueous emulsion or suspensoid antiperspirant preparations are disclosed which offer a cost advantage in addition to providing for the reduction or elimination of whitening of the skin, reduced tack and added emolliency.

5 Claims, No Drawings

NON-WHITENING ANTIPERSPIRANT COMPOSITIONS

BACKGROUND OF THE INVENTION

This invention relates to aqueous antiperspirant systems such as lotions and cream emulsions.

Numerous antiperspirant compositions are known and have been published in a variety of cosmetic journals as well as the patent literature and by suppliers of cosmetic ingredients. Those skilled in the art have accepted the fact that anhydrous suspension and emulsion silicone based antiperspirant systems are advantageous and have good consumer acceptance primarily due to the application and aesthetic qualities imparted by the silicone emollient; in addition, volatile silicone containing compositions offer an acceptable degree of antiperspirant effectiveness. The development of anhydrous and aqueous antiperspirant compositions have been reported and exemplified in several U.S. Patents, such as, U.S. Pat. No. 3,798,317; U.S. Pat. No. 2,955,983; U.S. Pat. No. 3,359,169; U.S. Pat. No. 3,420,932; U.S. Pat. No. 3,509,253; U.S. Pat. No. 3,816,613; U.S. Pat. No. 3,863,005 and U.S. Pat. No. 3,873,686.

Water based stick systems are described in U.S. Pat. Nos. 2,732,327; 2,857,315; 3,255,082; and 3,928,557. In these systems the antiperspirant active ingredient are solubilized in a thickened composition.

Anhydrous stick compositions, wherein the active ingredient is suspended, are disclosed in U.S. Pat. Nos. 4,049,792; 4,126,679; 4,151,272; and 4,435,382.

Suspension and emulsion antiperspirant roll-on and cream compositions are disclosed in U.S. Pat. Nos. 4,083,956; 4,264,586; 4,499,069; and in GB 2018590A, all silicone containing compositions.

Aerosolized antiperspirant compositions containing volatile silicones, utilized in part to improve their effectiveness and reduce staining have been reported in the patent and non patent literature. It must also be noted that alcohol based antiperspirant sticks and roll-ons have been described in U.S. Pat. Nos. 4,137,306 and 4,435,382. These forms of antiperspirant, in addition to having the tendency of exhibiting a lower degree of effectiveness are often irritating to the skin, and particularly for the latter reason, have never been successfully marketed.

In order to overcome the shortcomings of known antiperspirant compositions, in either suspension or emulsion roll-on forms, it is an object of the present invention to replace, in total, the volatile silicone component with other liquid ingredients, specifically polydimethyl siloxanes.

The need for such replacement is primarily to lower the cost of silicone containing formulations, impart added emolliency to the system, yet retain the same aesthetic characteristics normally attributed to the silicones, such as feel to the skin, low irritation, low degree of staining, compatibility while retaining antiperspirant effectiveness and reducing or eliminating the whitening of the skin, a negative attribute of existing volatile silicone formulations.

SUMMARY OF THE DISCLOSURE

The present invention relates to antiperspirant compositions wherein the antiperspirant active ingredient is delivered to the skin by means of an aqueous suspension or emulsion roll-on. More specifically, the present invention relates to an effective, highly aesthetic, reduced whitening, low cost compositions comprising from about 10% to about 60% by weight of a water soluble antiperspirant salt, from about 1% to about 30% by weight of one or more water insoluble or dispersible emulsifiable waxes, from about 2% to about 20% by weight polydimethyl siloxane and up to about 70% by weight of deionized water.

The compositions may optionally contain from about 0% to 40% by weight of one or more water insoluble liquid organic emollients from about 0% to about 10% of finely divided inert filler materials; from about 0% to 5% by weight of surface active agents; from about 0% to about 5% of suspending agents; and from about 0% to about 2% of bactericidal agents, skin protectants, fragrance oil and colorants.

Inert fillers can be selected from talc, fumed silica, starch and clays.

Emulsifiable waxes, emulsifiers and surface active agents may be selected, preferentially from a group of non ionic ethers and esters such as those known to the trade under the tradenames Brij 30, Brij 35, Tween 20, Tween 80, Arlacel 165, Brij 72, and Brij 721, propylene glycol stearates, Kesco Glycerol esters, Pluronic and Tetronics, ethoxylated stearyl alcohol, the ethoxylated or propoxylated lanolin alcohols and compounds thereof, such as the trademarked products Span 65, Arlamol E, etc.

The preferred emulsifiers are the polyethylene glycol fatty alcohol ethers particularly the stearyl alcohol ethers identified as steareth "n" wherein n represents the average number of ethylene oxide units in the polyethylene glycol segment.

It is further optional to have in the composition of this invention suspending agents such as Silica, Bentone and/or Magnesium Aluminum Silicate.

The present compositions may also contain as an optional ingredient, one or more emollient materials of organic nature and selected from among those that have a low degree of irritation and/or toxicity and that provide a softening soothing effect to the skin surface. A preferred organic emollient material is (2,5-Dioxo-4-imidazolidinyl)urea commonly known as allantoin.

Examples of astringent salts, in the form of aqueous solutions or spray-dried impalpable particles, ingredients that produce a reduction in sweat by physiological action upon delivery to axillae area, are aluminum chlorohydrate, aluminum sesquichlorohydrate, aluminum zirconium chlorohydrates with and/or without buffer, sodium aluminum lactate and chlorohydroxy lactate, among others known to the trade.

In accordance with the present invention, silicones such as dimethyl polysiloxane, cyclic dimethyl polysiloxane are added to the compositions in order to provide compositions having a low degree of irritation and toxicity and provide a softening or soothing effect on surface skin while reducing or eliminating the whitening effect, a negative attribute of existing volatile silicone formulations. A preferred polysiloxane material is dimethicone. These materials when used in antiperspirant compositions of the present invention afford highly aesthetic, non-whitening, and effective lower cost formulations.

The following examples are given to further illustrate the present invention. It is to be understood that the invention is not limited thereto.

EXAMPLES 1-4

| Ingredient | 1 % WW | 2 % WW | 3 % WW | 4 % WW |
| --- | --- | --- | --- | --- |
| D.I. Water | 55.50 | 51.50 | 52.50 | 55.00 |
| Aluminum Chlorohydrate 50% acq. sol | 40.00 | 40.00 | 44.00 | 40.00 |
| Steareth-2 | 1.50 | 2.00 | 1.00 | 1.50 |
| Steareth-21 | 1.00 | 1.00 | 1.00 | 1.00 |
| Dimethicone | 2.00 | 5.00 | 1.50 | 2.50 |
| Allantoin | — | 0.50 | — | — |
| Perfume | qs | qs | qs | qs |
|  | 100.00% | 100.00% | 100.00% | 100.00% |

The preceding specific embodiments are illustrative only of the practice of the invention. It is to be understood, however, that other expedients known to those skilled in the art, or disclosed herein, may be employed without departing from the spirit of the invention or the scope of the appended claims.

What is claimed is:

1. Aqueous non-whitening, non-staining antiperspirant composition consisting essentially of:
   (a) from about 1% to about 30% by weight of an emulsifier selected from the group consisting of propylene glycol stearates and ethoxylated stearyl alcohol;
   (b) from about 2% to about 20% by weight of linear non-volatile dimethicone;
   (c) from about 10% to about 60% by weight of a water soluble antiperspirant salt; and
   (d) up to about 70% by weight water.

2. The composition of claim 1 wherein said emulsifier is an ethoxylated stearyl alcohol.

3. The composition of claim 1 wherein said water soluble antiperspirant salt is an aluminum salt.

4. The composition of claim 3 wherein said aluminum salt is aluminum chlorohydrate.

5. The composition of claim 4 including from about 0.5% to about 1.5% by weight (2,5-dioxo-4-imidazolidinyl)urea.

* * * * *